United States Patent [19]

Riggs

[11] Patent Number: 4,636,272
[45] Date of Patent: Jan. 13, 1987

[54] PROCESS FOR THERMALLY BONDING PLASTIC TUBES

[75] Inventor: Gary T. Riggs, West Palm Beach, Fla.

[73] Assignee: Cordis Corporation, Miami, Fla.

[21] Appl. No.: 702,945

[22] Filed: Feb. 19, 1985

[51] Int. Cl.$^4$ .............................................. B29C 65/02
[52] U.S. Cl. ...................................... 156/158; 156/86; 156/309.6
[58] Field of Search ............ 156/158, 159, 157, 304.2, 156/304.6, 86, 304.3, 294, 293, 309.6, 311; 604/280, 283, 905

[56] References Cited

U.S. PATENT DOCUMENTS

| | | | |
|---|---|---|---|
| Re. 30,817 | 12/1981 | Loyd et al. | 156/86 |
| 3,467,561 | 9/1969 | Waride | 156/49 |
| 3,832,253 | 8/1974 | DiPalma et al. | 156/86 |
| 3,861,972 | 1/1975 | Glover et al. | 156/86 |
| 3,972,548 | 8/1976 | Rosean | 156/304.3 |
| 4,003,382 | 1/1977 | Dyke | 128/349 B |
| 4,092,193 | 5/1978 | Brooks | 156/86 |
| 4,251,305 | 2/1981 | Becker et al. | 156/86 |
| 4,263,236 | 4/1981 | Briggs et al. | 264/26 |

FOREIGN PATENT DOCUMENTS 0036169 3/1977 Japan .................................. 156/158

Primary Examiner—Michael Ball
Attorney, Agent, or Firm—Henry W. Collins; Thomas R. Vigil

[57] ABSTRACT

The process for thermally bonding plastics is capable of bonding two tubings over a very small circumferential overlap area and the bond formed thereby, is able to withstand high peel and shear forces. The method includes the steps of: providing a stepped mandrel having a smaller diameter portion and a larger diameter portion; sliding a first tubing over the smaller portion; sliding a second tubing over the larger portion and slightly over the first tubing to establish an overlapping area to be bonded; sliding a shrink tubing over the second tubing to a position over the overlapping area; placing the overlapping area in a die; and heating the die a sufficient amount for a sufficient time to cause bonding of the first tubing to the second tubing. Preferably, the first tubing is made of a substantially non-crosslinked olefin and the second tubing is made of a highly crosslinked (heat shrink) polyolefin.

25 Claims, 8 Drawing Figures

PROCESS FOR THERMALLY BONDING PLASTIC TUBES

BACKGROUND OF THE INVENTION

1. Field of the Invention

The present invention relates to a process for thermally bonding plastic parts which are not amenable to adhesive bonding. More particularly, the invention relates to a process for thermally bonding plastic parts, such as two polyolefinic substrates, e.g., tubings, one of which is highly crosslinked, to produce a bond of narrow width over a predetermined circumscribed area which has high strength against peeling or shearing.

2. Description of the Prior Art

Heretofore the bonding of plastic tubings, such as the bonding of a crosslinked plastic tubing to a non-crosslinked plastic tubing, has been accomplished utilizing conventional thermal bonding or adhesive bonding processes.

The adhesive bonding process utilizes an epoxy or structured acrylic which may cause a reduced strength against peeling attributable to loosening of the seal or to a loss of adhesiveness of the epoxy or acrylic due to environmental attack on, or aging of, the adhesive.

Conventional thermal bonding processes require the application of heat to areas of a tubing greater than one inch in length. Such large areas over which the heat is applied commonly contain "hot spots" and the heating of such a large area can result in an uneven shrinking or splitting of one tubing relative to another tubing which are being bonded together during cooldown of the tubings after bonding.

Various processes for bonding plastics are disclosed in the following U.S. Patents:

| U.S. Pat. No. | PATENTEE |
| --- | --- |
| 3,467,561 | Waride |
| 3,832,253 | DiPalma, et al. |
| 4,003,382 | Dyke |
| 4,251,305 | Becker, et al. |
| 4,263,236 | Briggs, et al. |
| Re. 30,817 | Loyd, et al. |

The Waride U.S. Pat. No. 3,467,561 discloses a method of insulating a joint formed in a conductor or electrical cable by applying a first winding of heat fusible synthetic plastic tape over the joint and a second winding of tetrafluoroethylene tape and then heating the tape windings for unification.

The DiPalma et al. U.S. Pat. No. 3,832,253 discloses a method of making an inflatable balloon catheter wherein a number of heat shrinkable sleeves and adhesive are utilized to attach a catheter tip to a catheter shaft.

The Dyke U.S. Pat. No. 4,033,382 discloses a method of forming a retention catheter wherein a thermoplastic polyurethane body is bonded to a thermosetting polyurethane balloon. The thermosetting polyurethane balloon sleeve is molded with integral bands of a thermoplastic polyurethane polymer spaced at either end of the sleeve and is sealed to the body by fusing the thermoplastic polyurethane polymer bands to the body by application of heat or solvent.

The Becker, et al. U.S. Pat. No. 4,251,305 discloses a method and apparatus for the radiant heat sealing of a balloon onto a catheter, the method employing the use of tinted shrink tubing sections in areas to be bonded and the apparatus being automatic to provide heat to the areas along the catheter to be bonded for short periods of time while feeding the catheter automatically into the machine for the bonding.

The Briggs, et al. U.S. Pat. No. 4,263,236 discloses a method for forming a catheter with an inflation cuff. The catheter is formed of a thermoplastic material while the cuff is formed of an elastomeric material which is not thermoplastic. Once the cuff is placed over the catheter, pressure is directed inwardly around the entire periphery of at least each end of the cuff while the catheter is being heated sufficiently to soften same so as to enable at least the ends of the cuff to be recessed into the material of the catheter by the inwardly directed pressure.

The Loyd, et al. U.S. Reissue Pat. No. Re. 30,817 discloses a method of applying a laminated tubular insulating connector for splicing or terminating electric conductors. The connector comprises an outer layer of a heat shrinkable dielectric material and an inner layer of a relatively soft, self-adhesive, low temperature flowable thermoplastic material. When heated, the outer layer shrinks and the inner layer functions as a sealant and cushioning agent.

The process of the present invention differs from the previously proposed methods by providing a narrow circumferential section of bonding between two tubings where intricate fittings are required, i.e., when special tips of materials different than the material from which a catheter tubing is made are required, and a very intimate contact between the tubings is formed by providing an inward compressive force during heating of the tubings with the resultant bond having increased strength against peeling or shearing as will be described in greater detail hereinafter.

SUMMARY OF THE INVENTION

According to the invention there is provided a process for thermally bonding together first and second tubings made of plastic and forming a bond in an area having a narrow width; said process comprising the steps of:

choosing a stepped mandrel wire having a small diameter portion the outer diameter of which corresponds to the inner diameter of the first plastic tubing to be utilized, a larger diameter portion having an outer diameter which corresponds to the inner diameter of the second plastic tubing to be utilized, and a shoulder separating the stepped portions;

feeding one end of a first plastic tubing over the small diameter portion of the mandrel wire;

feeding the end of the second plastic tubing over the larger diameter portion of the mandrel wire to a position where it overlaps the end of the first plastic tubing fed onto the small diameter portion of the mandrel wire from a direction opposite that in which the first plastic tubing was fed over the mandrel wire;

feeding a section of shrink tubing having an appropriate inner diameter to receive the first and second plastic tubings therein over the second plastic tubing to a position over where the overlapped first and second tubings are centrally located within the shrink tubing;

placing the plastic tubing assembly comprising the mandrel wire, one end of the first plastic tubing, one end of the second plastic tubing, and the shrink tubing into a specially configured preheated die assembly including chill blocks;

heating a narrow circumferential portion of the assembly to thermally bond the plastic tubings together;

allowing the heated tubing assembly to cool;

and after cooling, removing the shrink tubing and mandrel wire.

DESCRIPTION OF THE PREFERRED EMBODIMENT

Figure 1:
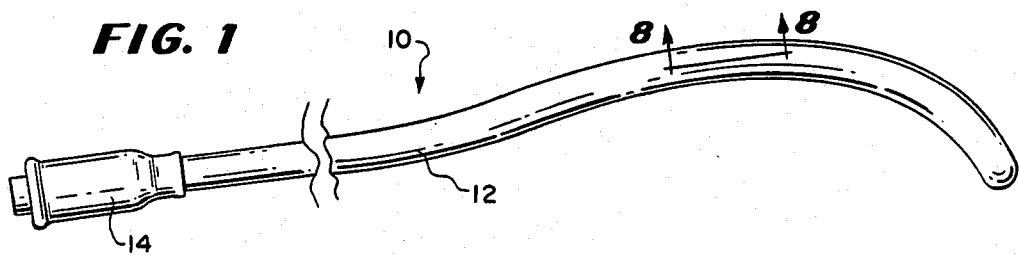
FIG. 1 is a side plan view of a catheter formed by the process of the present invention.

Referring now to the drawings in greater detail, there is illustrated in FIG. 1 a catheter 10 which is formed by the process of the present invention and which comprises a body 12. A hub 14 is shown attached to the proximal end of the catheter 10.

As will be described in greater detail below, the catheter 10 is formed from at least two tubings of different material to provide the catheter 10 with at least two areas having different characteristics and where the tubing materials utilized are not amendable to adhesive bonding. In this respect, the process is particularly useful where it is desired to provide a special tip made of one plastic material bonded to a catheter body made of another material and where a good bond is required which can withstand high peel and/or shear forces.

For example, the bonding process of the present invention can be used to create a bond between two polyolefinic substrates. This bond is difficult to create utilizing conventional thermal bonding techniques and in cases where one of the substrates is a highly crosslinked (over 90%) polyolefin, the difficulty of creating a bond is multiplied.

The key to any bonding technique is the degree of intimate contact provided in the area of the bond. In cases where a highly crosslinked polyolefin substrate is utilized, this intimate contact becomes crucial to the formation of the bond since no admixture layer is provided in the highly crosslinked polyolefin material at the substrate bonding interface. The process of the present invention, as will be described in greater detail hereinafter, provides such intimate contact and thus a bond which will have great strength against peel and shear forces. Further, the bond is formed over a very small area, having a width of no more than 1-6 mm, thus reducing the chances of forming "hot spots" on the tubing.

Figure 2:
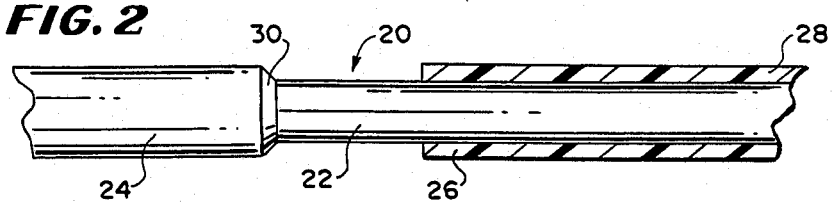
FIG. 2 is a longitudinal sectional view of one end of a first plastic tubing being fed over a mandrel wire.

Turning now to FIG. 2, there is illustrated therein a mandrel wire 20 which is stepped to form a smaller in diameter portion 22 and a larger in diameter portion 24. Typically, this mandrel wire 20 is made of stainless steel which has a fluoropolymer coating thereon, preferably of polytetrafluoroethylene sold under the trademark Teflon by Dupont of Wilmington, Delaware. The mandrel wire 20 is provided to assure a constant diameter of the lumen of the catheter 10 during the formation thereof as will be described below. As shown, one end 26 of a first tubing 28 is fed over the thinner portion 22 of the mandrel wire 20 until it abuts a shoulder 30 of the mandrel wire 20 which flares to the thicker portion 24. The shoulder 30 serves to inhibit axial flow of the material from which the first tubing 28 is made during the subsequent thermal bonding.

The first tubing 28 can be made from a number of plastic materials, such as a polyester elastomer sold under the trademark Hytrel by Dupont of Wilmington, Delaware, or polyurethane, or and oriented polyester such as poly(ethylene-terephthalate) (PET). In a preferred embodiment, the first tubing 28 is made of Hytrel ™.

Prior to feeding the first tubing 28 over the mandrel wire 20, the inner and outer surfaces of the tubing 28 are degreased using degreasing solvents. One such degreasing solvent which can be utilized is sold under the trademark Freon TF by Dupont of Wilmington, Delaware.

The degreasing solvent and water absorbed during the degreasing process are allowed to evaporate prior to feeding the first tubing 28 over the mandrel wire 20 as well.

Figure 3:
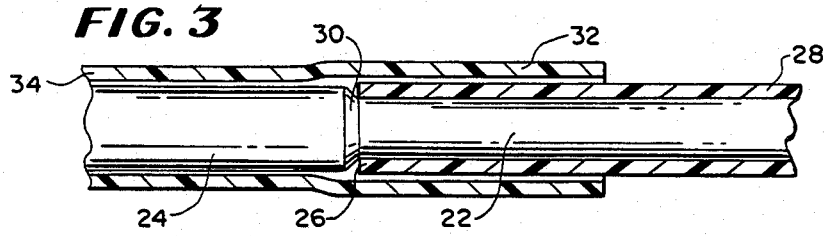
FIG. 3 is a longitudinal sectional view of a second plastic tubing being fed over the mandrel wire and the end of the first plastic tubing and into an overlapping relationship.

As illustrated in FIG. 3, an end 32 of a second tubing 34 is fed over the mandrel wire 20 from a direction opposite that from which the first tubing 28 was fed to a position where it overlaps the end 26 of the first tubing 28. In this FIG., the end 32 of the second tubing 34 is shown to be flared, with the flaring usually being no more than a ¼ inch taper. This flaring is only for the purposes of providing an internal diameter to the end 32 of the second tubing 34 which is greater than the external diameter of the end 26 of the first tubing 28 so that the second tubing 34 will fit over the first tubing 28 and, in circumstances where a second tubing 34 is utilized having an internal diameter greater than the external diameter of the first tubing 28, the flaring is not required.

The second tubing 34 may be made from any of the materials listed above from which the first tubing 28 can be made. In one embodiment, the second tubing 34 is preferably made of an oriented polyester such as the poly(ethylene-terephthalate) (PET) material. Preferably, the second tubing 34 is made of a cross-linked olefin (a heat shrink material) and must be pre-expanded to yield the following proportions: (a) an expanded inner diameter which is larger than the outer diameter of the first tubing 28 and (b) a recovered inner diameter which is approximately 80% of the first tubing's 28 outer diameter.

Figure 4:
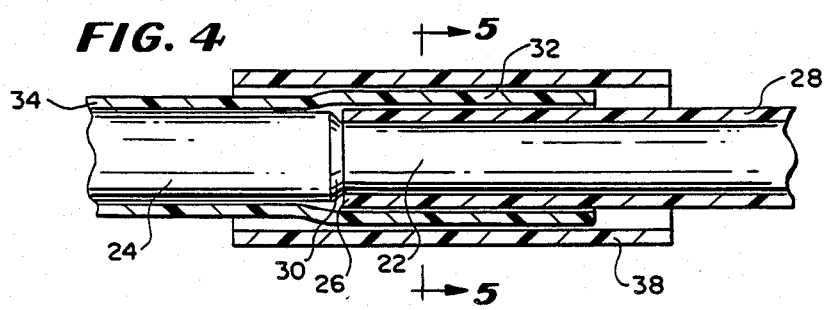
FIG. 4 is a longitudinal sectional view of the mandrel wire with overlapping ends of each plastic tubing received thereover and shows the placement of a shrink tubing over the section of overlap.

Turning now to FIG. 4, once the end 32 of the second tubing 34 is overlappingly positioned over the end 26 of the first tubing 28, a shrink tubing 38 is placed over the area of overlap of the tubings 28 and 34 in such a manner that the overlapping or flared end 32 of the second tubing 34 is centered within the shrink tubing 38. The shrink tubing 38 is typically made of a fluoropolymer such as polytetrafluoroethylene (PTFE or Teflon TM). The shrink tubing 38 must have an expanded inner diameter greater than the outer diameter of the second tubing 34 and must be capable of shrinking (recovering) to a diameter which equals approximately 80% of the outer diameter of the second tubing 34, with the area immediately adjacent to and including the end 32 of the second tubing 34 becoming a seal zone 39 (FIG. 8) as will be described in further detail hereinafter. It has been empirically determined that a section of shrink tubing 38 having an inner diameter before shrinking of approximately 0.093 inch and an outer diameter of approximately 0.136 inch is preferred for bonding tubings wherein the outer diameter of the second tubing 34 measures between approximately 0.089 inch and 0.092 inch.

Figure 5:
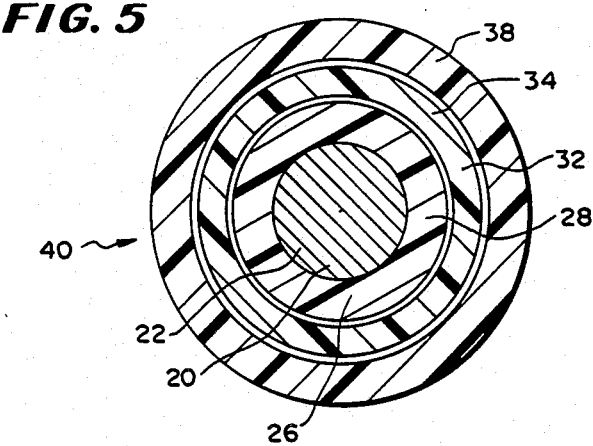
FIG. 5 is a cross sectional view through the area to be bonded and is taken along line 5—5 of FIG. 4.

As illustrated in FIG. 5, in cross section, the combination of the above elements provides a tubing assembly 40 in the area to be bonded prior to bonding comprising, from inside to outside, respectively, the mandrel wire 20, the end 26 of the first tubing 28, the end 32 of the second tubing 34, and the shrink tubing 38.

Figure 6:
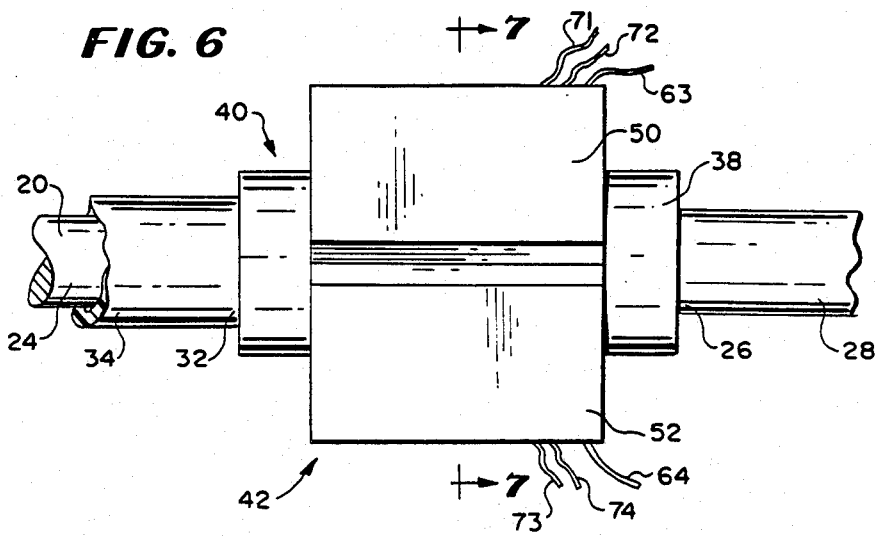
FIG. 6 is a side elevational view of the area to be bonded received within a die assembly of the present invention.

In FIG. 6, there is shown a side elevational view of the tubing assembly 40 centrally positioned within a die assembly 42 of the present invention.

As illustrated, the tubing assembly 40 is positioned in such a manner as to have a section of the shrink tubing 38 approximately ⅛ inch in length extending from each end of the die assembly 42 to the center of the tubing assembly 40 within the die assembly 42, with the shrink tubing 38 being only ½ inch long. The first tubing 28 extends from one end of the shrink tubing 38, the second tubing 34 extends from the other end of the shrink tubing 38, and the mandrel wire 20 is provided with a length sufficient to allow it to extend from both ends of the die assembly 42.

Figure 7:
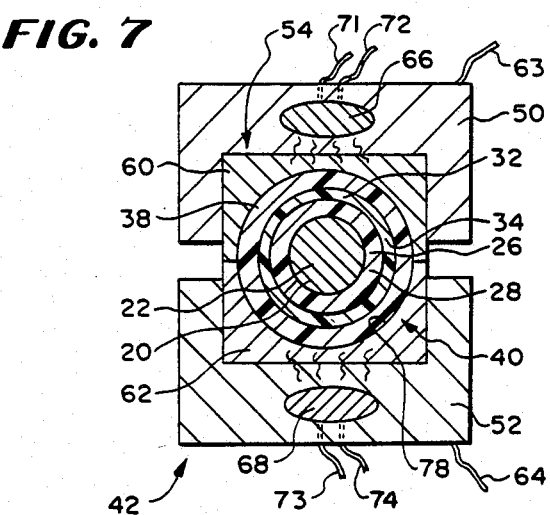
FIG. 7 is a cross sectional view through the die assembly and tubings received therein and is taken along line 6—6 of FIG. 5.

FIG. 7 is a cross sectional view through the die assembly 42 with tubing assembly 40 positioned therein and shows the die assembly 42 of the present invention. The die assembly 42 comprises two chill blocks 50 and 52 with a heating die 54 therein formed of two stainless steel, C-shaped sections 60 and 62 and is only ¼ inch in length to give the heating die 54 the capability of becoming heated quickly when electrical current supplied via conductor wires 63 and 64 flows through the chill blocks 50 and 52 and of cooling or chilling quickly when the current is stopped. Typically, current of 70 peak amps is provided over a 4 second time period to bring the temperature of the die 54 to over 700° F. An alternate method for heating the die 54 utilizes a heating element 66 and/or 68 mounted in each chill block 50, 52 and supplied via wires 71, 72 and/or 73, 74 with electric current.

The chill blocks 50 and 52 are made of copper and provide a heat sink to quicken dissipation of heat from the heating die 54 once current flow is stopped. In this respect, once the heating die 54 is preheated to a certain desired temperature prior to introduction of the tubing assembly 40 into the die assembly 42, heat will only be applied for a very short period of time to the tubing assembly 40, somewhere in the range of 4 seconds to 2 minutes and preferably for only 1 minute. Therefore, the heating die 54 must be able to cool quickly.

As illustrated, the heating die 54 includes the two identical C-shaped sections 60 and 62 which are sized to provide an interior compartment or cavity 78 to the heating die 54 which is sized to provide restrictive forces against outward expansion of the tubing assembly 40 during heating thereof and turns the forces created by the expansion inwardly against the mandrel wire 20.

In this respect, when electric current flows from the power supply to and through the heating die 54, the temperature of the heating die can be increased in a range from 430° F. to over 700° F. for causing shrinking of the shrink tube 38. Because of the constraints placed on the tubing assembly 40 by the heating die 54, the compressive forces developed from the shrinkage of the shrink tube 38 and the second tubing 34 when it is made of a heat shrink material are directed against the first tubing 28 and mandrel wire 20, respectively.

The first tubing 28, with the mandrel wire 20 therein, becomes molten due to the heat and compressive forces and is compressed against the inner wall of the second tubing 34. Further, during shrinking of the shrink tubing 38, the inner wall of the second tubing 34 becomes convoluted, during shrinking, and the compressive forces being applied by the heat and by the shrinkage of the shrink tubing 38 force the molten first tubing 28 into a 1:1 correspondence with the convoluted inner wall of the second tubing 34.

Figure 8:
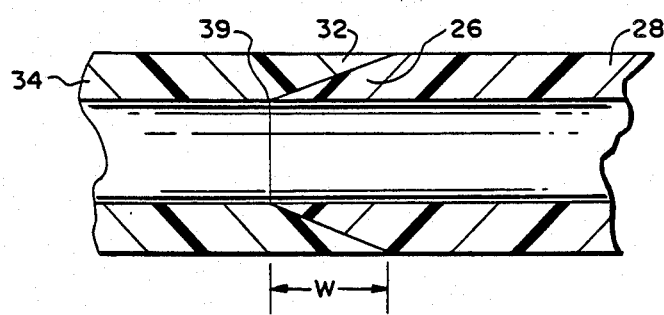
FIG. 8 is longitudinal sectional view through the area of the bond formed by the process of the present invention after heating, cooling and removal of the shrink tubing from the area of the bond and is taken along line 8—8 of FIG. 1.

Once the heating is stopped and the tubing assembly 40 is allowed to cool, the shrink tubing 38 is removed, the mandrel wire 20 is withdrawn, and a catheter 10 comprised of two different plastic materials as shown in FIG. 8 is formed. It is to be understood that the bonded area has a dimension of approximately 1-6 mm in width W (FIG. 8) and forms the seal zone 39 described above.

As defined above, the process of the present invention provides a very intimate bonding of the tubings 28 and 34 with the resultant bond having great strength against peeling and shearing. Further, since the width of the bonded area is approximately 1-6 mm, "hot spots" are not likely to be formed as those encountered where a bonded area has a width of ½ inch or more.

From the foregoing description, it will be apparent that the process for thermally bonding plastics of the present invention has a number of advantages, some of which have been described above and others of which are inherent in the invention. Also, it will be apparent to those skilled in the art that modifications can be made to the process of the present invention without departing from the teachings of the present invention. Accordingly, the scope of the invention is only to be limited as necessitated by the accompanying claims.

We claim:

1. A process for thermally bonding together first and second tubings made of a plastic material with a bond area having a narrow width; said process comprising the steps of:

providing a stepped mandrel wire having a small diameter portion the outer diameter of which corresponds to the inner diameter of the first plastic tubing to be utilized, a larger diameter portion having an outer diameter which corresponds generally to the outer diameter of the first plastic tubing, and a shoulder separating the stepped portions;

feeding one end of the first plastic tubing over the small diameter portion of the mandrel wire;

feeding the end of the second plastic tubing over the larger diameter portion of the mandrel wire to a position where it overlaps the end of the first plastic tubing fed onto the small diameter portion of the mandrel wire from a direction opposite that in which the first plastic tubing was fed over the mandrel wire;

feeding a section of shrink tubing having an inner diameter sufficient to be received over the second plastic tubing to a position where the overlapped first and second tubings are centrally located within the section of shrink tubing;

placing the plastic tubing assembly comprising the mandrel wire, one end of the first plastic tubing, one end of the second plastic tubing, and the shrink tubing into a specially configured preheated die assembly including chill blocks;

heating a narrow circumferential portion of the assembly to cause the shrink tubing section to shrink and force the second tubing against the first tubing which is being melted by the heating to thermally bond the plastic tubings together;

allowing the heated bonded tubings to cool;

and after cooling, removing the shrink tubing and mandrel wire.

2. The process of claim 1 wherein the end of said second tubing is flared if necessary to accommodate the end of the first tubing therein.

3. The process of claim 1 wherein said tubing is made of a polyolefinic material.

4. The process of claim 1 wherein said tubing is made of polyurethane.

5. The process of claim 1 wherein said tubing is made of a polyester elastomer.

6. The process of claim 1 wherein said tubing is made of an oriented polyester.

7. The process of claim 1 wherein said tubing is made of a high crosslinked (over 90%) polyolefin.

8. The process of claim 1 wherein said tubing is made of poly(ethylene-terephthalate).

9. The process of claim 1 wherein said mandrel wire is made of stainless steel.

10. The process of claim 1 wherein said stainless steel mandrel wire is coated with a fluoropolymer.

11. The process of claim 10 wherein said fluoropolymer coating is polytetrafluoroethylene.

12. The process of claim 1 wherein said shrink tubing is made of a fluoropolymer.

13. The process of claim 12 wherein said fluoropolymer is polytetrafluoroethylene.

14. The process of claim 1 wherein said first tubing is made of a substantially non-crosslinked olefin and said second tubing is made of a highly crosslinked polyolefin.

15. The process of claim 14 wherein said crosslinking of said plastic material of said second tubing is approximately 90%.

16. The process of claim 14 wherein said second tubing is pre-expanded to yield an expanded inner diameter larger than the first tubing's outer diameter and has a recovered inner diameter of approximately 80% of the first tubing's outer diameter.

17. The process of claim 14 wherein said section of shrink tubing has an expanded inner diameter greater than the outer diameter of the crosslinked second tubing and a recovered inner diameter which is approximately 80% of the outer diameter of the crosslinked second tubing.

18. The process of claim 1 wherein said second tubing has a very convoluted inner surface during heating and shrinking thereof.

19. The process of claim 1 wherein said narrow circumferential area being bonded is approximately 1 to 6 mm in width.

20. The process of claim 1 wherein the heat applied is in a range between 430° and 800° F.

21. The process of claim 20 wherein the heat applied is between 500° and 700° F.

22. The process of claim 1 wherein the heat is applied for between 4 seconds and 2 minutes.

23. The process of claim 22 wherein the heat is applied for approximately 1 minute.

24. The process of claim 1 wherein said die assembly is heated by applying a current of approximately 70 peak amps through the die for approximately four seconds.

25. The process of claim 1 wherein said die assembly is heated by heating elements embedded in the chill blocks of the die assembly.

* * * * *